United States Patent [19]

Fuller, Jr.

[11] Patent Number: 5,235,116
[45] Date of Patent: Aug. 10, 1993

[54] PROCESS FOR THE PREPARATION OF 2-(1-PHENYLETHYL)HYDROQUINONE AND 2-(1-PHENYLETHYL)HYDROQUINONE DIACETATE

[75] Inventor: Dewey W. Fuller, Jr., Bristol, Tenn.

[73] Assignee: Eastman Kodak Company, Rochester, N.Y.

[21] Appl. No.: 933,547

[22] Filed: Aug. 24, 1992

[51] Int. Cl.$^5$ .................. C07C 39/14; C07C 37/14
[52] U.S. Cl. .................. 568/744; 568/747; 568/763; 568/766
[58] Field of Search ............ 568/744, 747, 763, 766

[56] References Cited

U.S. PATENT DOCUMENTS

| | | | |
|---|---|---|---|
| 2,247,404 | 7/1941 | Perkins et al. | 568/744 |
| 2,432,356 | 12/1947 | Underwood | 568/744 |
| 2,506,410 | 5/1950 | Blake | 260/810 |
| 2,714,120 | 7/1955 | Kehe | 568/744 |
| 3,772,393 | 11/1973 | Hunter | 568/74 X |
| 4,600,765 | 7/1986 | Lee et al. | 528/193 |
| 4,661,645 | 4/1987 | Lee et al. | 568/744 |
| 4,734,531 | 3/1988 | Chang | 568/744 |
| 5,041,692 | 8/1991 | Ungarelli . | |

FOREIGN PATENT DOCUMENTS

| | | | |
|---|---|---|---|
| 0188535 | 11/1982 | Japan | 568/744 |
| 8912037 | 12/1989 | World Int. Prop. O. | 568/744 |

OTHER PUBLICATIONS

Hawthorne and Reintjes, Journal of the Am. Chem. Soc. 87(20), pp. 4585-4587 (1965), "The Preparation of Alkylhydroquinones by the Reductive Alkylation of Quinones with Trialkylboranes".

Primary Examiner—Werren B. Lone
Attorney, Agent, or Firm—Bernard J. Graves, Jr.; William P. Heath, Jr.

[57] ABSTRACT

Provided is an improved process for preparing 2-(1-phenylethyl)hydroquinone and its diacetate salt. In this process, the differential solubility of product and starting materials hydroquinone and styrene in non-polar organic solvents is utilized to provide mono-alkylated materials which can be easily removed from the reaction mixture. A solid acid catalyst is also used which allows the isolation of product and recycle of unreacted starting materials to be accomplished on an industrial-scale continuous process.

10 Claims, 2 Drawing Sheets

PROCESS FOR THE PREPARATION OF 2-(1-PHENYLETHYL)HYDROQUINONE AND 2-(1-PHENYLETHYL)HYDROQUINONE DIACETATE

FIELD OF THE INVENTION

This invention belongs to the field of synthetic organic chemistry. In particular, it relates to the synthesis of 2-(1-phenylethyl)hydroquinone and its diacetate salt.

BACKGROUND OF THE INVENTION

It is known that phenylethylhydroquinone can be prepared by the reaction of hydroquinone with styrene:

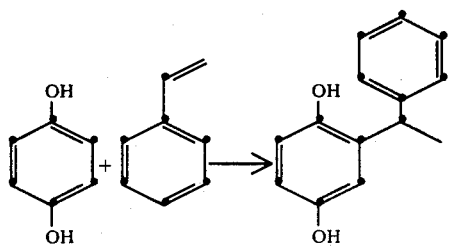

Methods for the preparation of phenylethylhydroquinone typically provide low yields due to excessive production of dialkylated hydroquinone. Further, the widespread use of corrosive acid catalysts such as sulfuric, hydrochloric, and para-toluene sulfonic acid demand the use of expensive corrosion-resistant reaction vessels. Such acids, of course, eventually require neutralization and disposal.

SUMMARY OF THE INVENTION

The present invention provides an improved process for preparing 2-(1-phenylethyl)hydroquinone and its diacetate salt. In this process, the differential solubility of product and starting materials hydroquinone and styrene in non-polar organic solvents is utilized to provide mono-alkylated materials which can be easily removed from the reaction mixture. A solid acid catalyst is also used which allows the isolation of product and recycle of unreacted starting materials to be accomplished on an industrial-scale continuous process.

DETAILED DESCRIPTION OF THE INVENTION

This invention provides an improved process for the preparation of phenylethylhydroquinone(PEHQ) and its diacetate. PEHQ is useful in making polyesters and is useful as an antioxidant. It is particularly valuble in the preparation of liquid crystalline polyesters.

The process of the present invention involves the alkylation of hydroquinone with styrene in a non-polar organic solvent, while using a solid acid catalyst. The non-polar organic solvent should be selected so as to preferentially solvate PEHQ more strongly than it solvates the hydroquinone starting material. In this fashion, differential solubility makes possible the recovery of unreacted hydroquinone by selective crystallization followed by filtration or centrifugation. Solid acid catalyst can be recovered and recycled with the hydroquinone while the filtrate containing the PEHQ can be acetylated without prior isolation.

In this process, suitable solvents are pure or mixed hydrocarbons and their ethers having a boiling point of >130° C. and a melting point of <70° C. Preferred non-polar solvents include xylenes, mesitylene, diphenyl ether, biphenyl, naphthalene, methyl naphthalene, dimethyl naphthalene, decahydronaphthalene (e.g., DECALIN), or a mixture thereof. Preferably the reaction is conducted at a temperature of about 70° C. to about 250° C.

Examples of suitable solid acid catalyst include, for example, acid form Molecular Sieves, AMBERLYST, clays such as kaolinite and montmoreillonite, mixed metal oxides such as $SiO_2/Al_2O_3$, $TiO_2/SiO_2$, $Al_2O_3/B_2O_3$, and the like, and mounted acids such as phosphoric acid and sulfuric acid on $SiO_2$. A preferred catalyst is silica alumina.

Figure 1:
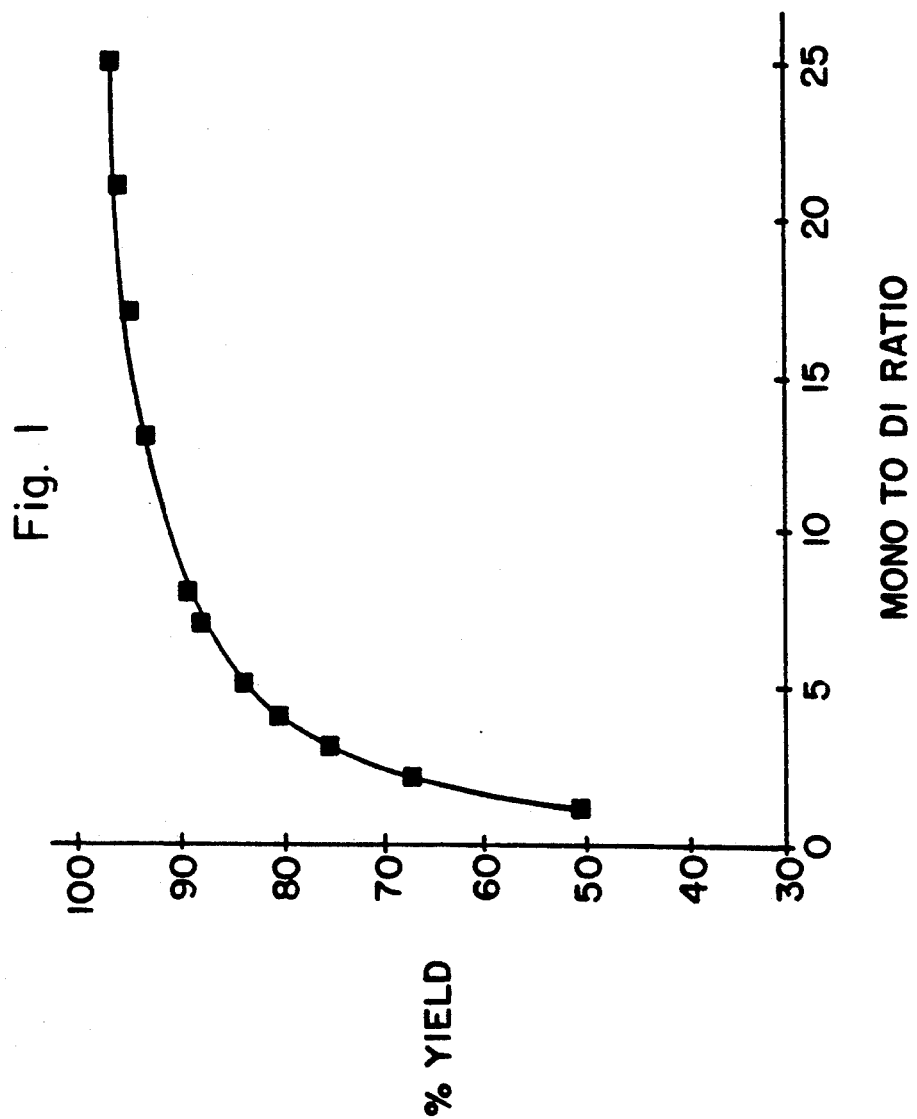
FIG. 1 is a plot of percentage yield in an alkylation reaction of hydroquinone with styrene versus the mono- to di-alkylation ratio of the products.
Figure 2:
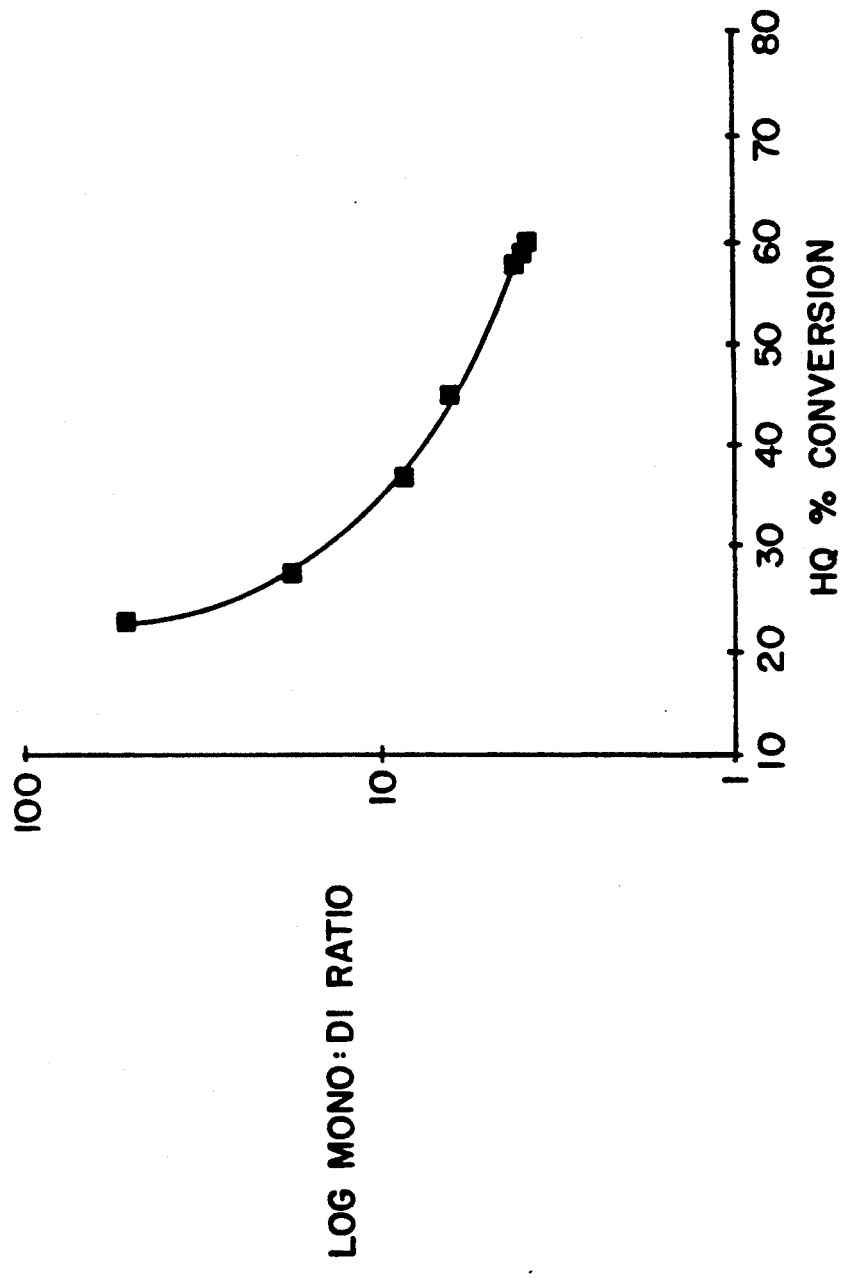
FIG. 2 is a plot of the log of the mono:dialkylated ratio versus the percentage of hydroquinone conversion.

Prior methodology has not provided the facile recovery of unreacted hydroquinone or catalyst. As shown below, the recovery of unreacted hydroquinone significantly improves the economics of operating at a lower conversion rate, where mono- to di- (alkylation) ratios are higher (see FIGS. 1 and 2 ). In the first example below, yield based on hydroquinone was increased from 47% to 74% by the recovery of hydroquinone in the filtration step. In the second example, yield was increased from 32% to 59%. Finally, as a further advantageous aspect of the present invention, the non-polor organic filtrate solution, which contains the desired PEHQ can be acylated without prior isolation of the PEHQ.

Thus, the present invention provides a continuous process for preparing 2-(1-phenylethyl)hydroquinone in a single reaction vessel, which comprises (a) continuously treating hydroquinone with styrene in a non polar organic solvent in the presence of a solid acid catalyst; followed by (b) continuously removing said phenylethylhydroquinone formed therein; and (c) continuously charging said reaction vessel with hydroquinone, styrene, and solid acid catalyst.

As a further aspect of the present invention, there is provided a process for preparing 2-(1-phenylethyl)hydroquinone which comprises treating hydroquinone with styrene in a non-polar organic solvent, in the presence of a solid acid catalyst.

EXPERIMENTAL SECTION

Example 1

Materials 600 grams Hydroquinone (Photographic Grade)
50 grams LZY-74 (UOP Zeolite)
2370 grams p-Xylene
454 grams Styrene
1068 grams Acetic Anhydride (Acetylation Grade)

The hydroquinone, LZY-74 zeolite, and p-xylene were charged to a 5 liter three neck flask equipped with nitrogen purge, overhead stirrer, and condenser. Styrene was added last with stirring. The slurry was stirred at reflux (138°–141° C.) 14.7 hours, then 7.3 grams extra LZY-74 were added. The slurry was stirred 1.5 hours additional at reflux before allowing to cool with stirring and was filtered at 60° C. Wet filter cake weighed 312 grams and assayed 71% hydroquinone.

Before adding anhydride, the filtrate was azeotropically dried by distilling off p-xylene. Acetylation was carried out by incremental addition of acetic anhydride while distilling over acetic acid and solvent. Remaining solvent was stripped off and the PEHQ-DA distilled through a 1" diameter column with 22" of Goodloe packing, at a pressure of 10 torr. Distilled PEHQ-DA assayed >99%. Taking into consideration the HQ recovered in the filter cake, yield based on HQ was 74%. Without the recovered HQ, yield would have been 47%.

Example 2

120 grams Hydroquinone (Photographic Grade)
10 grams $SiO_2/Al_2O_3$ Grade 970-08 (Grade)
500 grams Diphenylether
91 grams Styrene All of the above materials were stirred at 172°–194° C. for 2.5 hours. The reaction mix was allowed to cool with stirring to 90° C. before filtering. Wet filter cake weighed 97.06 g. and assayed 33.57% HQ. Yield based on HQ, if the filter cake material is taken into consideration, was 59%. Without the recovered HQ, yield would have been 32%.

I claim:

1. A continuous process for preparing 2-(1-phenylethyl)hydroquinone in a single reaction vessel, which comprises
    (a) continuously treating hydroquinone with styrene in a non-polar organic solvent selected from the group consisting of xylenes, mesitylene, biphenyl, naphthalene, methyl naphthalene, dimethyl naphthalene, and diphenyl ether, or a mixture thereof; in the presence of a solid acid catalyst selected from the group consisting of acid form Molecular Sieves, kaolinite, montmoreillonite, a mixed metal oxide selected from $SiO_2/Al_2O_3$, $TiO_2/SiO_2$, or $Al_2O_3/B_2O_3$, or a mounted acid; at a temperature of about 70° C. to about 250° C., followed by
    (b) continuously removing said 2-(1-phenylethyl)hydroquinone formed therein; and
    (c) continuously charging said reaction vessel with hydroquinone, styrene, and solid acid catalyst selected from the group consisting of acid form Molecular Sieves, kaolinite, montmoreillonite, a mixed metal oxide selected from $SiO_2/Al_2O_3$, $TiO_2/SiO_2$, or $Al_2O_3/B_2O_3$, or a mounted acid.

2. The process of claim 1, wherein the solid acid catalyst is amorphous silica aluminate.

3. The process of claim 1, wherein the solid acid catalyst is phosphoric acid or sulfuric acid on $SiO_2$, or wherein the solid acid catalyst is a mixture of phosphoric acid and sulfuric acid on $SiO_2$.

4. A process for preparing 2-(1-phenylethyl)hydroquinone which comprises treating hydroquinone with styrene in a non-polar organic solvent, in the presence of a solid acid catalyst.

5. The process of claim 4, wherein the non-polar organic solvent is selected from the group consisting of xylenes, mesitylene, diphenyl ether, biphenyl, naphthalene, methyl naphthalene, dimethyl naphthalene, and diphenyl ether, or a mixture thereof.

6. The process of claim 4, wherin the solid acid catalyst is selected from the group consisting of acid form Molecular Sieves, kaolinite, montmoreillonite, a mixed metal oxide selected from $SiO_2/Al_2O_3$, $TiO_2/SiO_2$, or $Al_2O_3/B_2O_3$, or a mounted acid.

7. The process of claim 4, wherein the solid acid catalyst is amorphous silica aluminate.

8. The process of claim 4, wherein the solid acid catalyst is phosphoric acid and/or sulfuric acid on $SiO_2$.

9. The process of claim 1, further comprising the additional step of reacting said 2-(1-phenylethyl)hydroquinone with acetic anhydride or a compound of the formula $CH_3C(O)$-X, wherein X is halo, to provide 2-(1-phenylethyl)hydroquinone diacetate.

10. The process of claim 4, further comprising the additional step of reacting said 2-(1-phenylethyl)hydroquinone with acetic anhydride or a compound of the formula $CH_3C(O)$-X, wherein X is halo, to provide 2-(1-phenylethyl)hydroquinone diacetate.

* * * * *